United States Patent [19]

Nakashima et al.

[11] Patent Number: 4,908,248
[45] Date of Patent: Mar. 13, 1990

[54] COOLING DEVICE FOR COOLING PARTS IN THE PROXIMITY THEREOF

[76] Inventors: Mitsuyoshi Nakashima, 11-11, Nagazumi 5-chome, Minami-ku, Fukuoka-shi, Japan; Satoshi Tsurusaki, 22-105, Natadanchi, Higashi-ku, Fukuoka-shi, Japan

[21] Appl. No.: 223,492

[22] Filed: Jul. 25, 1988

[30] Foreign Application Priority Data

May 19, 1988 [JP] Japan ............................... 63-66680[U]

[51] Int. Cl.$^4$ ............................................... F25D 3/08
[52] U.S. Cl. .................................... 428/355; 62/371; 62/530; 128/400; 128/402; 383/37; 383/901; 428/34.3; 428/58; 428/913
[58] Field of Search ................ 62/529, 530, 457, 371, 62/372, 457.9, 457.2, 457.4; 128/400, 402; 428/35.5, 913, 34.3, 58; 383/37, 901

[56] References Cited

U.S. PATENT DOCUMENTS

| | | | |
|---|---|---|---|
| 2,863,305 | 12/1958 | Shepherd | 62/530 |
| 4,174,598 | 11/1979 | Shepherd et al. | 62/530 |
| 4,324,111 | 4/1982 | Edwards | 62/530 |
| 4,592,358 | 6/1986 | Westplate | 62/530 |
| 4,676,247 | 6/1987 | Van Cleve | 62/530 |
| 4,741,176 | 5/1988 | Johnson et al. | 62/530 |

*Primary Examiner*—James J. Seidleck
*Attorney, Agent, or Firm*—Jordan and Hamburg

[57] ABSTRACT

A cooling device for cooling parts in the proximity thereof consisting of a single pouch or a plurality of continuous pouches, wherein each pouch has at least one face thereof being made of water-permeable material and has sealed therein a hygroscopically swelling material. Due to such construction, the sealed material of the cooling device in an unemployed state, i.e., before being chilled in a freezer or freezing compartment, is not hygroscopically swelled and is not voluminous so that it can be decreased in weight by reducing the quantity of the sealed material which can improve the transportation efficiency, resulting in lowered transportation costs. Furthermore, the device can be easily and securely attached to any body part or object such as the shoulder of a man or a beer bottle.

3 Claims, 9 Drawing Sheets

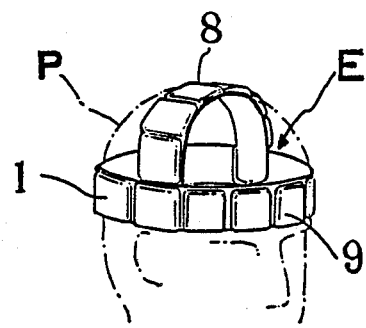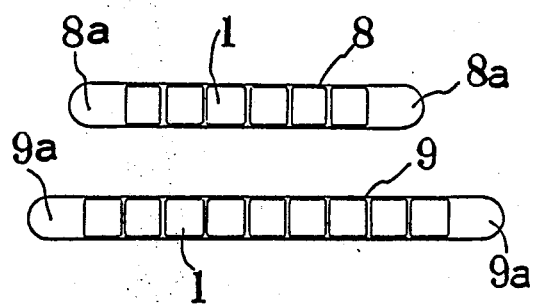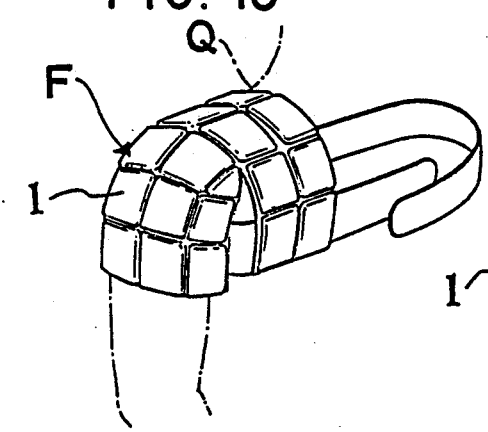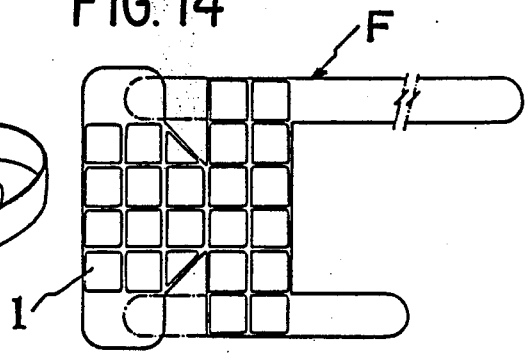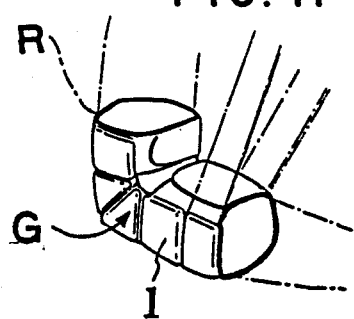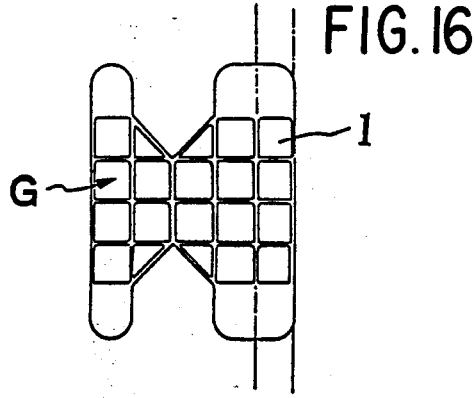

FIG. 19
FIG. 18
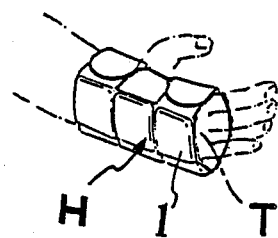
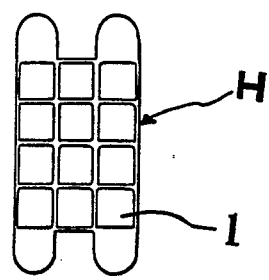
FIG. 21
FIG. 20
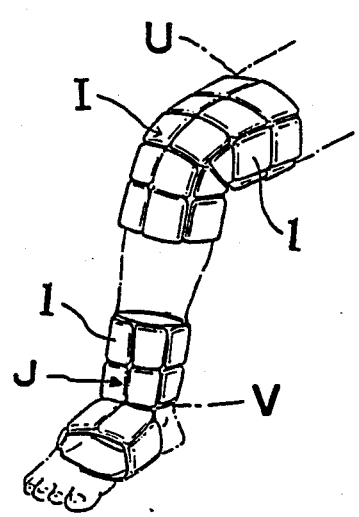
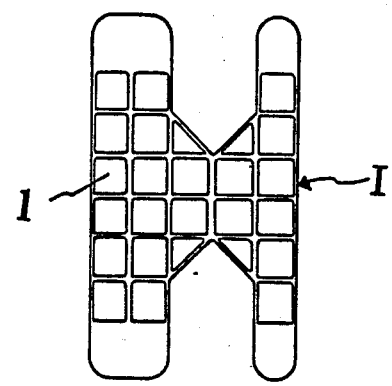
FIG. 22
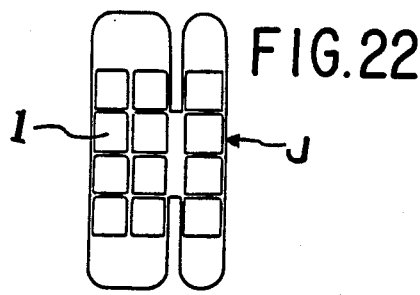

COOLING DEVICE FOR COOLING PARTS IN THE PROXIMITY THEREOF

BACKGROUND OF INVENTION

The present invention relates to a cooling device for cooling parts in the proximity thereof.

Conventional cooling devices used for cooling the head or some other affected part of the human body having a fever or in the summer to act against elevated temperatures and for preserving perishable foods by cooling or chilling consist of flexible cooling bags within which gel as a refrigerant is hermetically enclosed.

Such cooling devices, kept frozen in a freezer or freezing compartment, are taken out of the freezer or freezing compartment at such times as may be necessary.

Conventional cooling devices are made to have as large a volume of gel as possible so as to ensure sufficiently lengthened cooling time, making the devices voluminous and bulky which translates into added weight resulting in excessive or high transportation costs.

If the affected part to be cooled is a joint such as in a shoulder, elbow, or knee, conventional cooling devices have had such problems as inability to sufficiently cool the entire affected area.

On a cylindrical container such as a beer bottle or a mug that is to be cooled, the entire surface area of the object cannot be sufficiently covered and cooled.

Accordingly, it is an object of the present invention to provide a cooling device for cooling parts in the proximity thereof constituting a pouch, of which at least one face is made of water-permeable material, and having a hygroscopically swelling sealed material enclosed within the pouch.

It is also an object of the present invention to provide a cooling device for cooling parts in the proximity thereof consisting of a plurality of pouches, enclosing sealed material, connected in one direction and formed into one belt-shaped unit.

It is still another object of the present invention to provide a cooling device for cooling parts in the proximity thereof consisting of a plurality of pouches, enclosing sealed material, connected in two orthogonal directions and formed into one sheet-shaped unit.

When the cooling device is to be used, it is first soaked in water or ice water to allow the hygroscopically swelling sealed material in the pouch to swell, absorbing water through the side face of the pouch, of which at least one face is made of water-permeable material, and is then kept frozen in a freezer or freezer compartment in the above mentioned state, to be removed from the freezer or freezer compartment when necessary.

Here in the cooling device, frozen or solidified in the hygroscopically swelled and in its volumetrically enlarged state, the sealed material may sufficiently fulfill its role as a cooling device.

According to the object to be cooled or kept cooled, whether the head or another affected part of a human body, perishable foods, a beer bottle, or a mug, it can be effectively cooled or kept cooled either by being placed in direct contact with the cooling device consisting of a single pouch enclosing sealed material, or by being swathed by the cooling device consisting of a plurality of pouches, enclosing sealed material and being connected in one direction and formed into one belt-shaped unit, or by direct application of the cooling device consisting of a plurality of pouches enclosing sealed material and being connected in two orthogonal directions and formed into one sheet-shaped unit.

In keeping a cylindrical container such as a beer bottle or a mug cooled, the belt-shaped cooling device, swathed around the outer periphery of the container with both ends of the belt being bound by adhesive tapes, can be soaked in water or ice water allowing the sealed material to hygroscopically swell, then to be frozen in a freezer or freezing compartment.

In this operation, the cooling device is hygroscopically swelled and solidified after being swathed around the outer periphery of such a cylindrical container as a beer bottle or a mug, therefore, it can be firmly and securely attached around the outer periphery of the container, resulting in the elimination of such inconvenience as slipping out of the container while in service.

Due to the above-mentioned construction and operation, the present invention may bring about the following advantages:

(1) As the sealed material of the cooling device in an unemployed state before being cooled in a freezer or freezing compartment is not hygroscopically swelled and is not voluminous, it can be decreased in weight by reducing the quantity of the sealed material which can improve the transportation efficiency, resulting in lowered transportation costs.

(2) Because the cooling device is not voluminous as explained above in (1), it provides for a reduction of storage space and easier storage.

(3) When the affected parts to be cooled are joints such as in the shoulder, elbow, or knee, the adoption of the belt-shaped or sheet-shaped cooling device can provide a sufficient cooling over the entire affected part.

(4) Even when the object to be cooled or kept cooled is a cylindrical container such as a beer bottle or a mug, the adoption of the belt-shaped or sheet-shaped cooling device can securely cool or keep cooled the container by covering the outer peripheral surface.

BRIEF EXPLANATION OF DRAWINGS

FIG. 12~FIG. 24 are explanatory views of cooling devices as in the other embodiments.

BEST MODE FOR CARRYING OUT THE INVENTION

The cooling device of the present invention is described in detail in view of the preferred embodiments shown in the attached drawings.

Figure 1A:
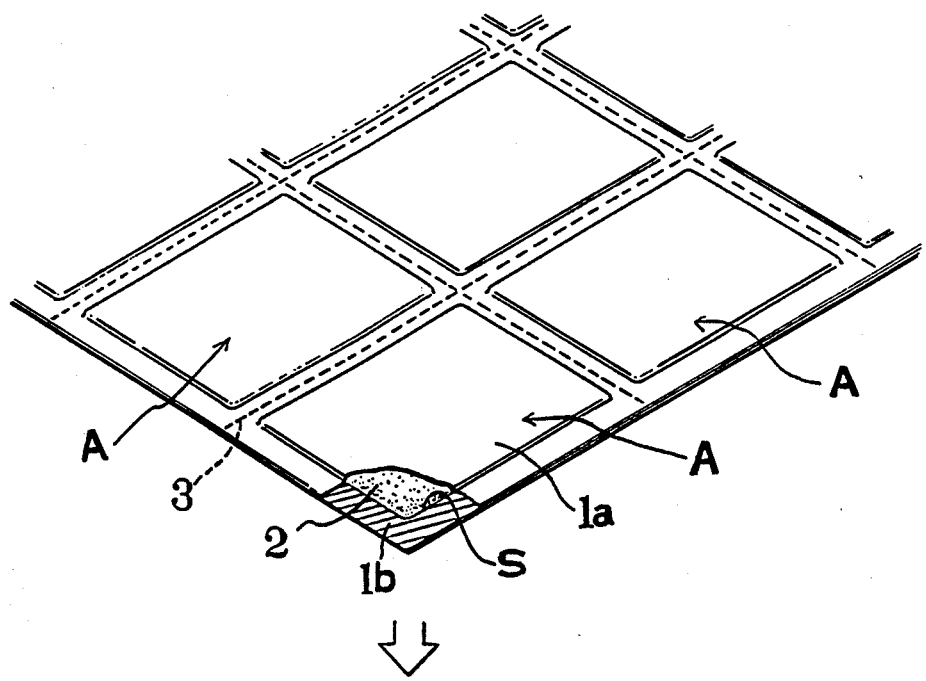
FIG. 1(a) is a perspective view with a partial cutaway of a cooling device relating to the present invention.
Figure 1B:
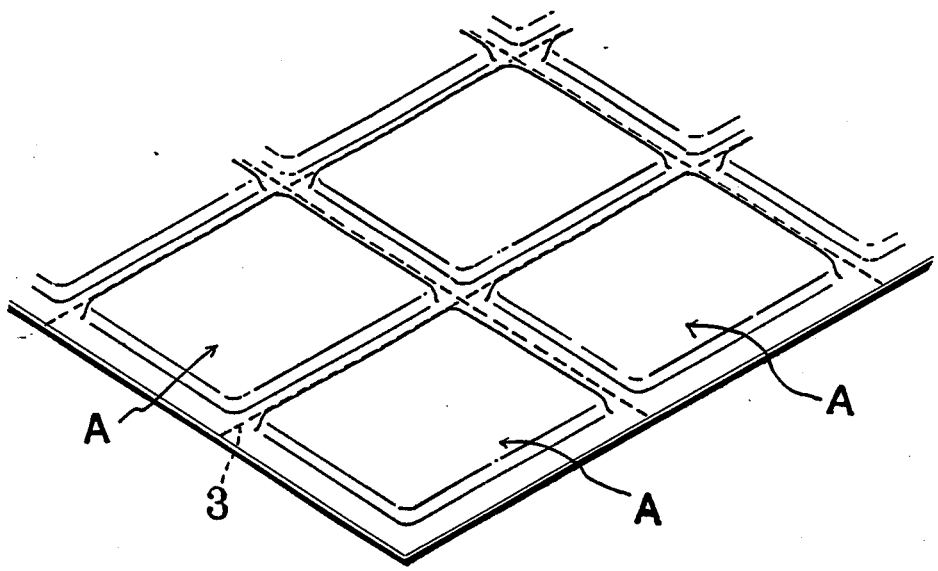
FIG. 1(b) is an explanatory perspective view showing the hygroscopically swelled state of the sealed material in the same cooling device as the above.

(A) shown in FIG. 1(a) and FIG. 1(b) is a cooling device related to the present invention. For making the cooling device (A), every margin of a rectangular sheet-shaped face (1a) which is made of water-permeable material that remains flexible even after chilled or cooled is overlapped and bonded with that of another face (1b) which is made of water-impermeable material that also remains flexible even after chilled or cooled to constitute a flat pouch (1). Such flat pouch (1) has a sealed space (S) inside and hygroscopically swelling sealed material (2) such as high molecular water-absorber or starch is filled or contained in the sealed space (S).

Herein, for the above mentioned water-permeable material, unwoven paper, an unwoven sheet formed by application of a special polyester and a special polypropylene, or unwoven sheet of polyester·polyethylene can be used.

ELEVIS (Registered Trademark of UNITIKA Ltd.), an unwoven fabric made of bicomponent fiber consisting of a polyester core and a polyethylene coating, can be effectively used as such water-permeable material.

And for the water-impermeable material, nylon-extensionless polypropylene or nylon-polyethylene can be employed.

For the hygroscopic polymeric agent, a crosslinked sodium polyacrylate can be used.

This embodiment includes a sheet cooling device formed by connecting a plurality of rectangular cooling devices (A) into one unit and having perforated lines (3) along every seam so that the sheet cooling device may serve as either a sheet as it is, or separating the sheet into a longitudinal or transverse row or belt, or separating the sheet into a single and individual pouch unit.

FIG. 1(a) shows the state in which the sealed material (2) is not hygroscopically swelled, whereas FIG. 1(b) shows the state in which the sealed material (2) is hygroscopically swelled by having soaked the cooling device (A) in water or ice water.

Furthermore, both sides of the pouch (1) can be formed also with water-permeable material.

Figure 2:
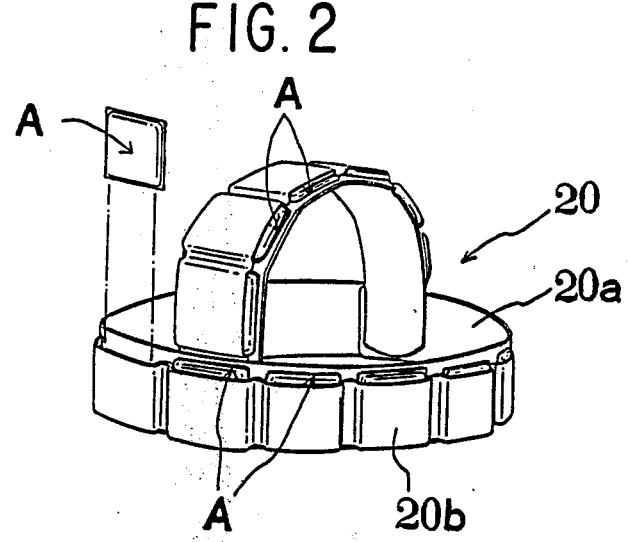
FIG. 2~FIG. 5 are explanatory views of the same cooling device as the above in service condition.
Figure 3:
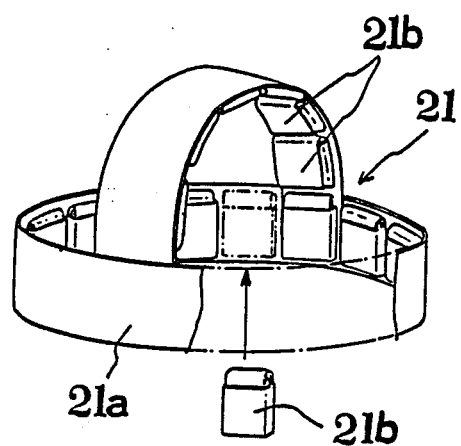

For cooling the human head with the cooling device (A) described above, it can be used in such a way as, for example, attaching it to the first or second head bands (20)(21) shown in FIG. 2 and FIG. 3.

The first head band (20) is provided with, on the outer periphery of the head band unit (20a), a plurality of cooling device attachment sections (20b) so that a cooling device (A) can be easily and readily placed into and removed from each attachment section (20b).

Figure 4:
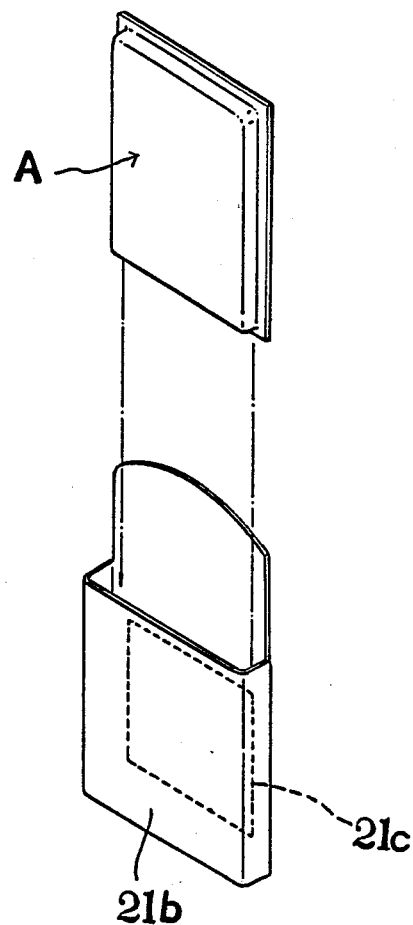
Figure 5:
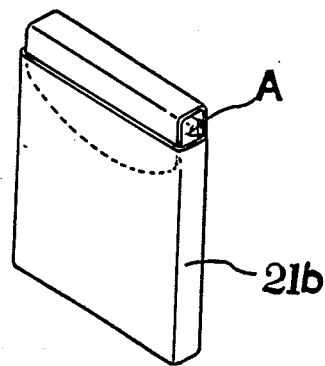
Figure 6:
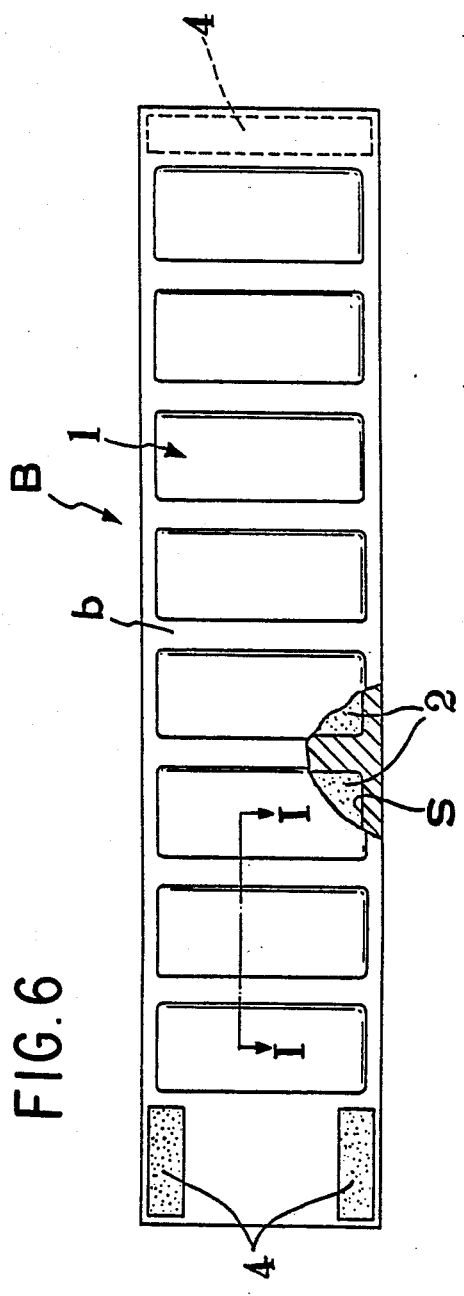
FIG. 6 is a front elevation view with a partial cutaway of a cooling device as in another embodiment.
Figure 7:
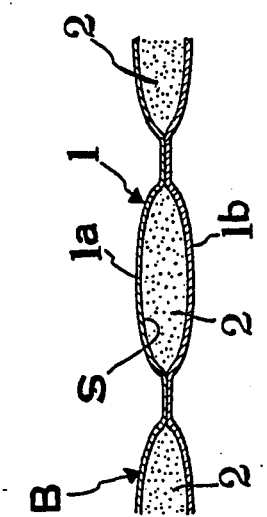
FIG. 7 is a sectional view of the cooling device of FIG. 6 taken along the line 1—1 of FIG. 6.

The second head band (21) is provided with, on the inner periphery of the head band unit (21a), a plurality of cooling device attachment sacks or pockets (21b) which can be easily and readily mounted and removed and in these attachment sacks (21b) a cooling device (A) can be enclosed as illustrated in FIG. 4 and FIG. 5 (21c).

In FIG. 4, an adhesive piece (21c) such as bonding tape is provided on the side wall of the cooling device attachment sack (21b).

(B) and (C) in FIG. 6~FIG. 8, FIG. 10 and FIG. 11 are the belt-shaped cooling devices related to the present invention.

In these cooling devices, a plurality of pouches (1) enclosing the sealed material (2) are transversely connected to constitute one belt-shaped cooling device unit (b)(c), and at both ends of the cooling device unit (b), adhesives (4) as face fasteners or adhesive tapes are provided.

Figure 11:
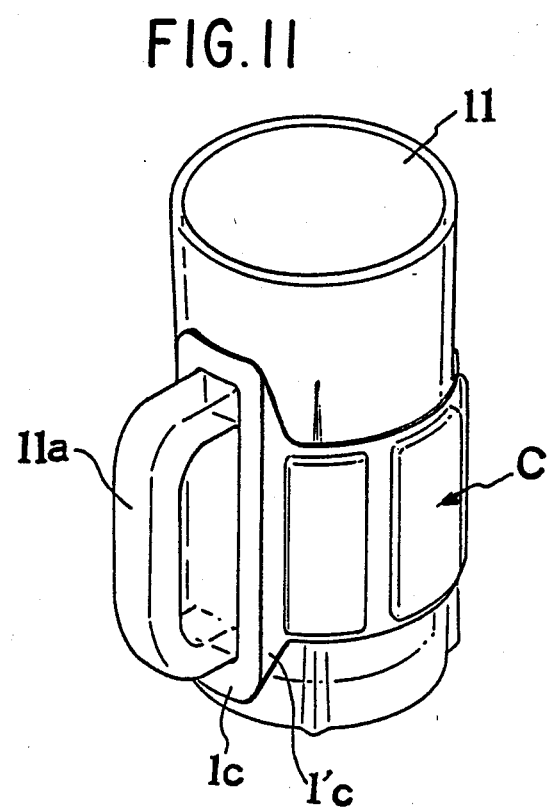
FIG. 11 is an explanatory view of the same cooling device as the above in service condition.

At both ends of the cooling device unit (c), ring-shaped attachment ear portions (1c) (1c') are provided, and such portions are made into one piece with the unit (c) that can be fit and engaged with the handle or grip (11a) of the mug (11) shown in FIG. 11.

Figure 8:
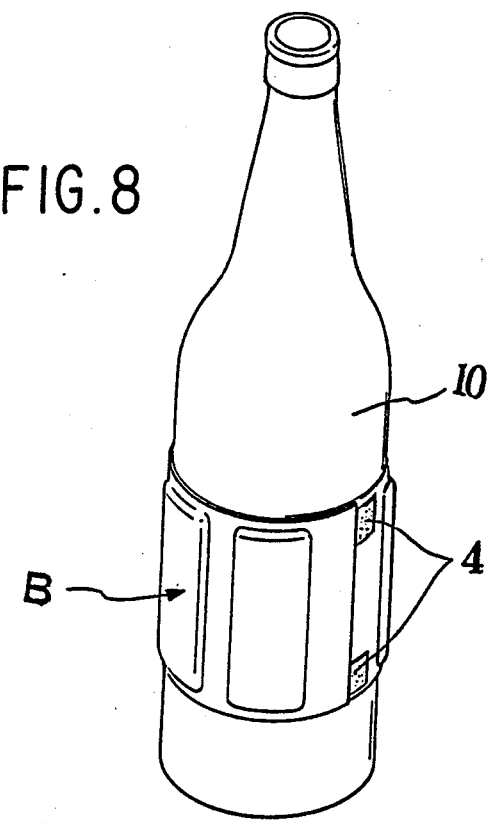
FIG. 8 is an explanatory view of the same cooling device as the above in service condition.

The cooling device (B) is so constructed as to be swathed on and readily attached to the outer periphery of a cylindrical container such as a beer bottle (10), as seen in FIG. 8.

The cooling device (C) is so constructed as to be swathed around and attached to the mug (11), as seen in FIG. 11.

Figure 9:
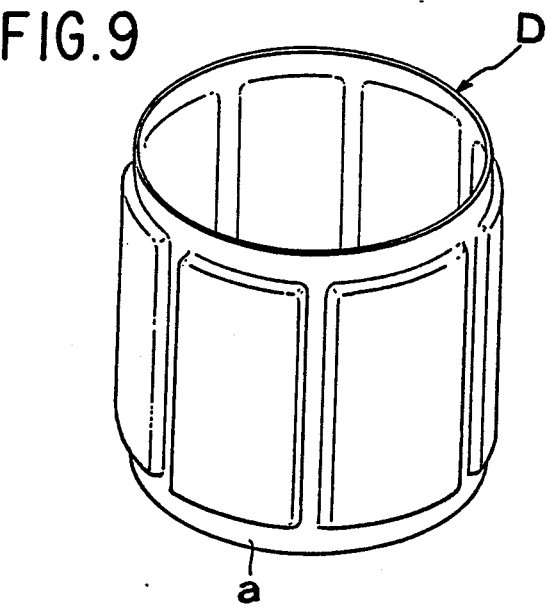
FIG. 9 is a perspective view of a cooling device as in the other embodiment.
Figure 10:
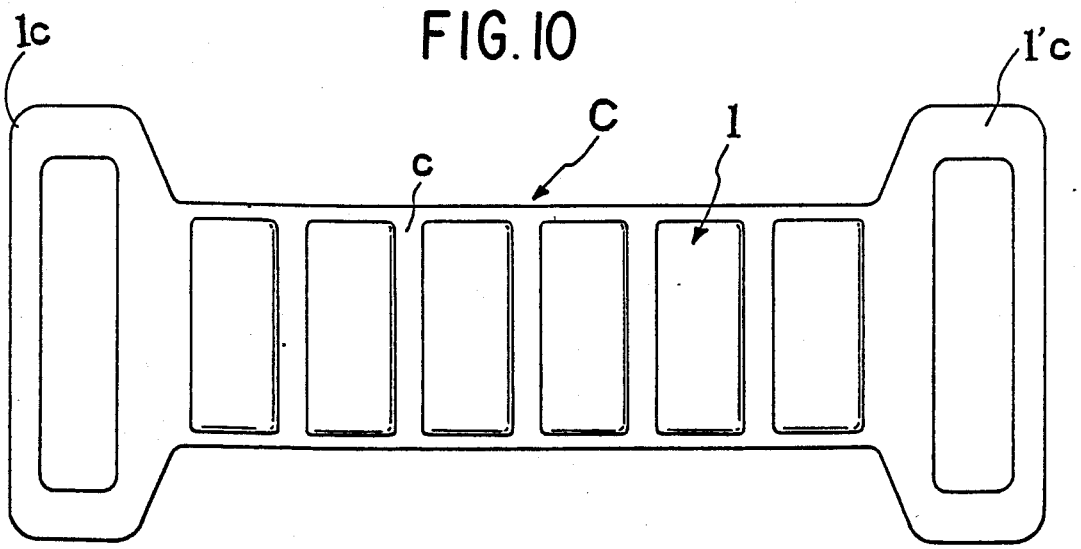
FIG. 10 is a front elevation view of a cooling device as in another embodiment.

(D) in FIG. 9 is a cooling device in the other embodiment, in which both ends of the above mentioned cooling device unit (a) are connected to constitute one ring shaped piece and the inner diameter is designed to be the same or slightly larger than the outer diameter of the cylindrical container or beer bottle (10) and so forth so that the device can be easily fitted and engaged with the cylindrical container.

And it is also possible to provide advertising by having messages or slogans printed on the above mentioned cooling devices (B)(C)(D) and to enhance the appearance by adding ornamentation or accessories such as ribbons or the like.

The (E) in FIG. 12 and FIG. 13 is another embodiment of the cooling device which consists of the first and second cooling devices (8)(9) and such cooling devices (8)(9) respectively have an adhesive part (8a)(9a) at both ends respectively where adhesive tapes or the like are provided. Accordingly, the cooling devices (8)(9) can be swathed and attached on the human head (P).

The (F)(G)(H)(I)(J)(K) in FIG. 14~FIG. 24 are sheet-shaped cooling devices relating to the present invention.

The cooling device (F)(G)(H)(I)(J) respectively consists of a plurality of pouches (1), within which sealed material (2) is enclosed, wherein the pouches (1) are connected in both longitudinal and transverse directions and formed into one sheet-shaped unit. The cooling device is also made to be bent to fit along the affected part of a human body such as a shoulder(Q), elbow (R), back of hand (T), knee (U), or ankle (V).

Furthermore, respective cooling device (F)(G)(H)(I)(J) is provided with adhesives such as adhesive tapes at the both ends so that the ends can be connected to each other.

Figure 23:
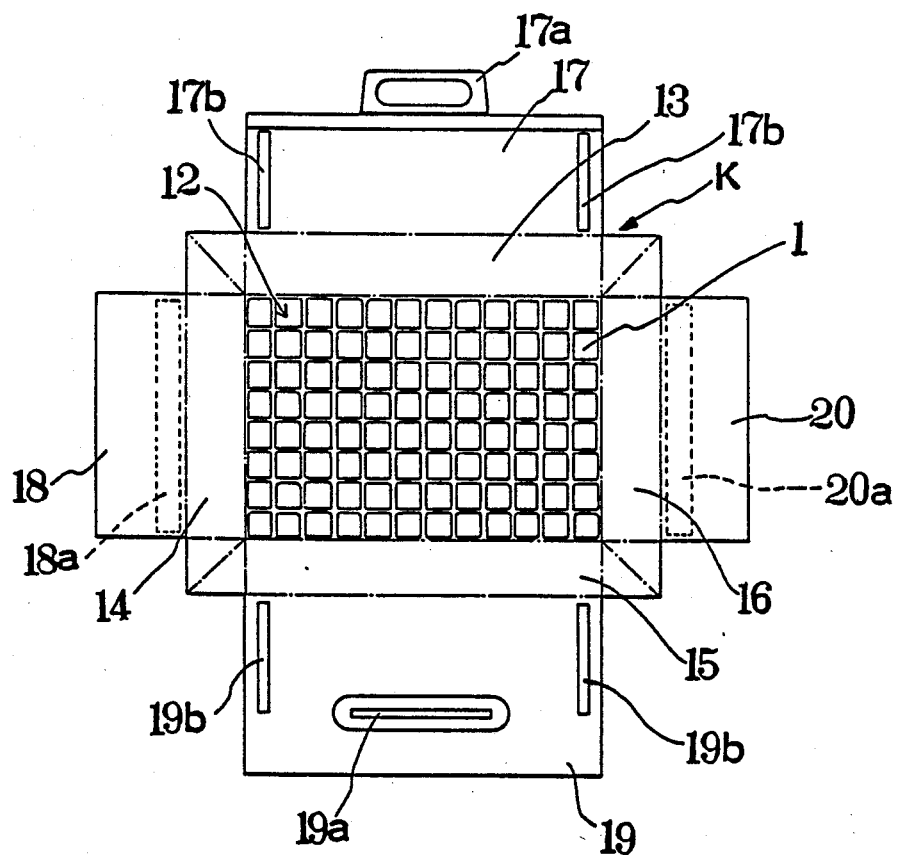

The cooling device (K), as shown in FIG. 23, consists of a rectangular sheet-shaped bottom part (12) which is formed by a plurality of pouches (1) and sealed material (2) is enclosed in each pouch (1). The pouches (1) are connected in both longitudinal and transverse directions into one unit. The side wall parts (13)(14)(15) thereof are attached, in such a way that they can be easily and readily bent, to the surrounding margins of said bottom part (12) into one unit with the bottom, and top wall parts (17)(18)(19) (20), respectively attached, in such a way that they can be easily and readily bent, to the corresponding side wall parts (13)(14)(15) (16) into one unit with the side walls, and is provided with a handle (17a) on one top wall part (17), a handle slit (19a) on the another to wall part (19) corresponding to the top part (17), and adhesives (17b)(18a)(19b)(20a) such as face fasteners of adhesive tapes on the inside or outside faces of respective top wall parts (17)(18)(19)(20).

Figure 24:
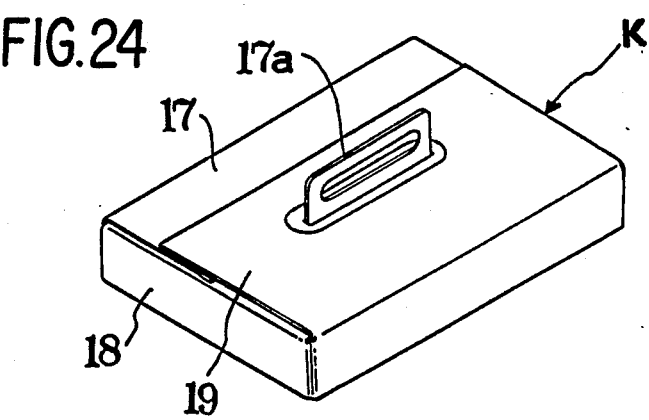

The cooling device (K) is of such construction that it can be assembled into a box by bending or folding the respective side wall parts and top wall parts, as shown in FIG. 24 and can be used as a cooling box.

The above-mentioned adhesives (17b)(18a)(19b)(20a) are positioned to mutually overlap when the top wall parts are bent or folded so that the box can be easily assembled and disassembled.

The embodiments of these devices are constructed as described above.

In using the cooling device (A), it is to be soaked in water or ice water beforehand to allow the sealed material (2) within the pouch (1) to hygroscopically swell, absorbing water through the face of the pouch (1) which is made of water-permeable material and to be frozen in a freezer or freezing compartment in that hygroscopically swelled state and to be taken out for use as necessary for cooling or maintaining cooled perishable foods or cooling the human head (P).

Here in the cooling device (A), the sealed material (2) is frozen or solidified in a hygroscopically swelled and volumetrically enlarged state thereby providing a long-time cooling effect.

The cooling devices (E)(F)(G)(H)(I)(J)(K) may be used in the same manner as previously stated. The cooling devices (E)(F)(G)(H)(I)(J) are effectively applicable for affected parts of the body especially for joint areas, and so constructed as to be easily and securely applied.

The cooling device (K) is useful as a cooling preserving box which can be carried with ease while containing fresh fish etc.

The cooling devices (B)(D) are useful by attaching when such cylindrical containers as beer bottles (10) are to be cooled or kept cooled, while the cooling device (C) is to be used for mugs (11) for effectiveness.

In using the cooling devices (B)(C)(D), the devices (B)(C)(D) as attached to a beer bottle (10) or a mug (11) are soaked in water or ice water to allow the sealed material (2) enclosed in pouches (1) to hygroscopically swell, then the beer bottle (10) or the mug (11), in this state, may be kept in a freezer to be taken out when necessary.

And as the cooling devices (B)(C) or (D) are allowed to hygroscopically swell then soldify after being swathed on the outer periphery of a beer bottle (10) or a mug (11), they can therefore be attached securely onto the outer periphery of said mug (11) or the like causing no such inconvenience as slipping while being used.

Moreover, if drops of water condense or collect on the outer surface of the beer bottle (10) or the mug (11) and drip or run down the side of said bottle or mug, the cooling devices (B)(D) and (C) can absorb the water drops and prevent water drops from dripping down to the bottom of the mug (11) etc. , due to the absorption capacity of the sealed material (2), which eliminates such inconvenience as water drops collecting on the table on which said mug (11) or the like is placed.

According to these embodiments, the following advantages may be found:

(1) Because the sealed material (2) of the cooling device (A)~(K) in an unemployed state before being chilled in a freezer or freezing compartment is not hygroscopically swelled and is not voluminous, it can be decreased in weight by reducing the quantity of the sealed material (2) which can improve the transportation efficiency, resulting in lowered transportation costs.

(2) Because the cooling devices (A)~(K) are not voluminous as explained in the above 1), they provide for a reduction of the storage space and easier storage.

(3) When the affected parts to be cooled are joints such as in the shoulder (Q), elbow (R), or knee (S), the adoption of the belt-shaped or sheet-shaped cooling device (E)(F)(G)(H)(I)(J) can provide sufficient cooling over the entire affected part.

And those devices can be easily and securely attached by simply joining the adhesive parts provided on the ends of the respective devices to one another.

(4) Even when the object to be kept cooled is a cylindrical container such as a beer bottle (10) or a mug (11), the adoption of the belt-shaped or sheet-shaped cooling device (B)(C) or (D) can securely keep the container cool covering the outer peripheral surface.

(5) Since the cooling device (K) can be folded and assembled into a box, it can be carried containing such objects to be cooled as or kept cooled fresh fish and so forth.

We claim:

1. A cooling device for cooling an object or body part in proximity thereto, said cooling device including a cooling bag comprising a pouch constituted of a pair of opposed walls, one of said walls being made of water impermeable sheet and the other of said walls being made of water permeable sheet capable of infiltrating water into said pouch by merely immersing said pouch in water, said opposed walls having the entire peripheries thereof completely bonded together to form a space between said opposed walls, and a filling of hygroscopically swellable material in a powder form in said space of said pouch, said material being capable of swelling by absorbing water which is infiltrated into said space of said pouch through said wall made of water permeable sheet by merely immersing said pouch in water.

2. A cooling device according to claim 1, comprising a plurality of said cooling bags, said cooling bags being interconnected linearly to form a flexible belt-shaped unit.

3. A cooling device according to claim 1, comprising a plurality of said cooling bags, said cooling bags being interconnected in two orthogonal directions to form a sheet-shaped unit which is flexible in both said directions.

* * * * *